United States Patent [19]

Wintermantel et al.

[11] Patent Number: 4,493,719
[45] Date of Patent: Jan. 15, 1985

[54] METHOD OF SEPARATION BY FRACTIONAL CRYSTALLIZATION FROM A LIQUID MIXTURE

[75] Inventors: Klaus Wintermantel, Dossenheim; Dieter Stockburger, Gruenstadt; Hugo Fuchs, Ludwigshafen, all of Fed. Rep. of Germany

[73] Assignee: BASF Aktiengesellschaft, Fed. Rep. of Germany

[21] Appl. No.: 479,005

[22] Filed: Mar. 25, 1983

Related U.S. Application Data

[63] Continuation of Ser. No. 764,536, Feb. 1, 1977, abandoned.

[30] Foreign Application Priority Data

Feb. 18, 1976 [DE] Fed. Rep. of Germany ....... 2606364

[51] Int. Cl.³ .............................................. B01D 9/02
[52] U.S. Cl. .................................. 62/532; 23/295 R
[58] Field of Search .................................. 62/532–543; 23/295 R

[56] References Cited

FOREIGN PATENT DOCUMENTS 1083850 9/1967 United Kingdom .

Primary Examiner—Frank Sever
Attorney, Agent, or Firm—Keil & Weinkauf

[57] ABSTRACT

A method of separation by fractional crystallization from a liquid mixture in which the liquid mixture is repeatedly passed in turbulent flow through an indirectly cooled crystallization zone, which must be kept full. The liquid remaining after deposition of a layer of crystals on the wall of the crystallization zone is removed, whereupon the surface of the layer of crystals is washed and the crystals are melted by passing a melt of similar compositions to that of the layer of crystals through the crystallization zone. During crystallization the melt is maintained at the temperature of crystallization and crystallization is stopped when the frozen fraction is from 70 to 98%.

5 Claims, 1 Drawing Figure

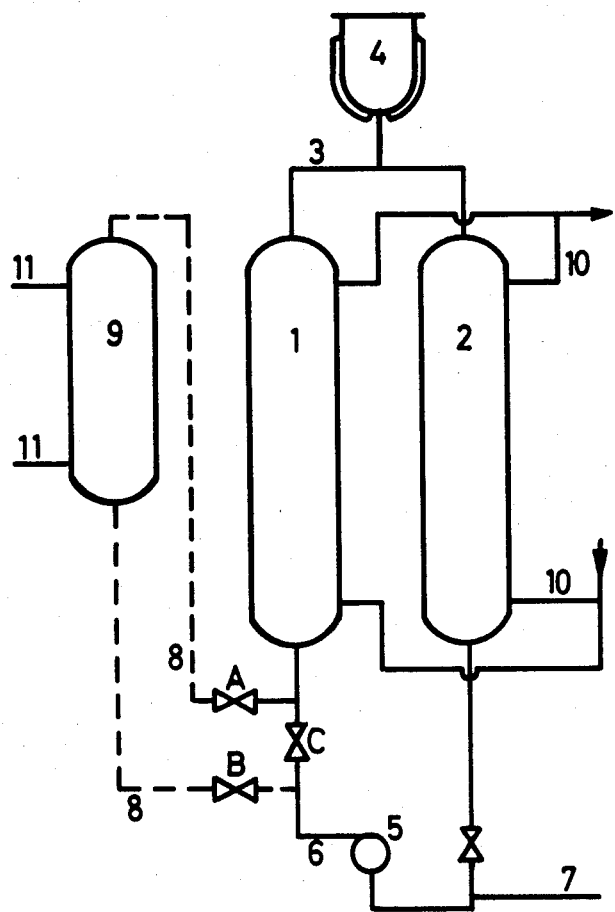

METHOD OF SEPARATION BY FRACTIONAL CRYSTALLIZATION FROM A LIQUID MIXTURE

This is a continuation of application Ser. No. 764,536 filed Feb. 1, 1977, now abandoned.

The present invention relates to a method of separation by fractional crystallization from a liquid mixture, in which the liquid mixture is repeatedly passed in turbulent flow through indirectly cooled crystallization zones, which must be kept full, the liquid remaining after deposition of a layer of crystals on the wall of the crystallization zone being removed, whereupon the surface of the layer of crystals is washed and the crystals are melted by passing a melt of similar composition to that of the layer of crystals through the crystallization zone. The invention also relates to apparatus for carrying out the above process.

German Laid-Open Application DOS No. 1,620,756 discloses a method of separation by crystallization in which crystallization is carried out in a column and the slurry of crystals formed is separated from the residual liquid by means of a sieve, the crystals then being fractionally melted. This process has the drawback that the separation of liquid and crystals requires mechanical means which are subject to breakdown.

According to U.K. Pat. No. 1,083,850, fractional crystallization is carried out by passing the melt a number of times through a cooled tube, removing the residual liquid and melting the crystals. During this process the melt is heated continuously in order to obtain a smooth crystal surface. However, this has the drawback that of necessity more of the layer of crystals is melted away at the top of the crystallization tube than at the bottom and consequently a funnel-shaped layer of crystals is formed. The different thicknesses of the layer of crystals cause variations in the heat-transfer which in turn have a deterimental effect on the crystallization. German Laid-Open Application DOS No. 1,769,123 describes a process in which the melt to be crystallized is passed through crystallization zones in the form of a trickling film. In this latter process, the layer of crystals is melted at its surface at intervals, and this again leads to the above disadvantages.

We have now found an improved method of separation by fractional crystallization from a liquid mixture in which the liquid mixture is repeatedly passed in turbulent flow through an indirectly cooled crystallization zone, which musst be kept full, the liquid remaining after deposition of a layer of crystals on the wall of the crystallization zone then being removed, whereupon the surface of the layer of crystals is washed and the crystals are melted by passing through the crystallization zone a melt of similar composition to that of the layer of crystals, in which method during crystallization the melt is maintained at the temperature of crystallization and crystallization is continued until the frozen fraction is from 70 to 98%.

The invention also relates to apparatus for carrying out separations by fractional crystallization comprising indirectly cooled tube systems having an inlet and outlet and characterized by two vertical parallel tubes or bundles of tubes acting as crystallizers, which are connected at the top by a pipeline to which a surge vessel is connected and which are connected at the bottom to form a loop via a pipeline containing the inlet and outlet, a heat exchanger being provided in a side loop on the pressure side of the pump.

The novel process has the advantage that uniform growth of the layer of crystals in the crystallization zones is achieved. Another advantage is that the surface area of the layer of crystals is kept to a minimum, which means a reduction in the amount of impurities adhering thereto. The amount of adhering impurities is also reduced by the fact that no storage vessel is required for the system and there is thus obtained a favorable ratio of crystallized material to remaining liquid.

We prefer to start from melts or solutions of the materials to be purified. We particularly prefer to sart from melts containing solvent, for example up to 25% by weight. Fractional crystallization from the melt has achieved particular commercial significance. Suitable compounds for said separation are organic compounds which have a melting point of from $-50°$ to $+200°$ C. and which do not decompose at the temperatures used. Examples of suitable compounds are dicyanobutene, adipodinitrile, hexamethylenediamine, methylene diisocyanate, dimethyldithiophosphorylacetic acid methylamide, naphthalene, naphthol, naphthyl acetate, xylene and acrylic acid. The melt crystallization of caprolactam, adipodinitrile and hexamethylenediamine has achieved particular industrial significance.

The crystallization zones may be in the form of tubes or polygonal channels. Tubular crystallization zones are preferred industrially, these being advantageously arranged in bundles in the form of heat exchangers. The crystallization zones advantageously have a diameter of from 1 to 4 cm and an 1/d ratio of from 100:1 to 1,000:1. Cooling of the crystallization zones may be effected by gases or advantageously by suitable liquid coolants such as water or cooling brine or evaporating refrigerants (eg. fluoro-chloromethane).

The liquid mixture to be crystallized is repeatedly recycled through the crystallization zone, which must be completely full at all times. Care must also be taken to ensure that the flow of liquid through the crystallization zone is a turbulent one. It has been found advantageous, therefore, to cause the liquid mixture to flow through the crystallization zones at velocities of from 0.2 to 6 m/sec.

An important feature of the invention is that the temperature of the liquid mixture is maintained at the given temperature of crystallization throughout the entire crystallization process. Thus the temperature is close to, ie. equal to or less than, the equilibrium temperature. It has been found to be particularly advantageous to ensure that, by appropriate control of the coolant temperature, the ratio of the rate of growth to the mass transfer coefficient at the interface during the freezing phase is maintained constant or caused to decrease. It has also been found advantageous to maintain a rate of growth of from 0.05 to 0.5 mm/min during crystallization. It will be appreciated that the rate of growth, once set at a value between these limits, is maintained as constant as possible.

Another important feature of the invention is that crystallization is carried out in the crystallization zone until the frozen fraction is from 70 to 98% and in particular from 80 to 95%. The frozen fraction is measured on the contents of a tube in the static state, the percentage given indicating the proportion of crystalline product. The frozen fraction is thus defined by the percentage of the cross-section of the tube which is filled out with crystalline product.

Once the desired frozen fraction has been achieved, cooling of the crystallization zones is stopped and the remaining liquid is removed from the loop. To remove adhering impurities, the surface of the crystalline material is washed with a liquid mixture, advantageously one having the composition of the starting mixture. The crystalline product is then melted by passing a melt of the substance to be crystallized through the crystallization zones. Of course, the melt must have a similar composition to that of the layer of crystalline product.

In order to achieve adequate purification, it is frequently necessary to connect several crystallization cycles to each other, the crystalline product of one cycle being used in the next.

It is particularly advantageous to cascade two crystallization zones such that the liquid mixture rises in the first zone and descends in the second zone. This gives an extremely favorable ratio of crystalline product to residual liquid.

BRIEF DESCRIPTION OF THE DRAWING

Suitable apparatus is illustrated in FIG. 1 by way of Example.

Two parallel vertical tubes or bundles of tubes (1) and (2) are interconnected at the top by a line (3) containing a surge vessel (4). At the bottom, the heat exchangers (1) and (2) are looped by a line (6) containing a pump (5). The inlet and outlet (7) is connected to the pipeline (6). On the pressure side of the pump (5) in pipeline (6), a heat exchanger (9) is contained in a side loop via lines (8). The lines (10) indicate inlets and outlets for the coolant and the lines (11) inlets and outlets for the heating medium, the reference letters A, B and C indicating valves.

The method of the invention is carried out, for example, as follows:

From a storage vessel (not shown), a suitable melt, for example a melt of caprolactam, is passed through inlet (7) to the cycle consisting of pump (5), lines (6), heat exchangers (1) and (2) and line (3), the valves to the heat exchanger (9) being closed. A portion of the melts collects in the surge vessel (4). The pump (5) continuously recycles the melt at the rates given and the coolant is passed through lines (10) at such a rate as to give the aforementioned conditions. When the frozen fraction in the heat exchangers (1) and (2) is from 70 to 98%, the residual melt is removed through line (7) to a receiver (not shown). During this discharge operation, the melt contained in the surge vessel (4) washes the surface of the layer of crystalline product in the heat exchangers (1) and (2) and the surfaces (3), (6) and (5) not coated with crystalline product. A melt having the same composition as the crystalline product is then passed through the inlet (7), the valve C being closed whilst valves A and B are open so that the heat exchanger (9) is included in the loop. The melt is circulated through the system, the heat exchanger (9) being heated to such an extent that the layer of crystalline product in the heat exchangers (1) and (2) is melted. The melt is then discharged through line (7) to a storage vessel (not shown).

If further purifying stages are necessary, the purified melt thus obtained is used for the next cycle and so on until the desired degree of purity has been achieved.

The method of the invention is suitable for purifying liquid and particularly molten mixtures, for example mixtures containing caprolactam.

The method of the invention is illustrated below with reference to the following Examples.

EXAMPLE 1

Apparatus as shown in FIG. 1 is used, the heat exchangers (1) and (2) each consisting of a tube having a length of 5 m and an internal diameter of 25 mm and enclosed by a heating jacket. The loop consisting of heat exchangers, tubes and pumps has a capacity of 8.8 l. The system is filled with 8.8 l of molten caprolactam having a solidifying point of 68.0° C., a color number of more than 1,000 APHA and a content of 4.0 meq/kg of volatile bases. The melt is circulated through the system, cooled to about 68° C. and maintained at that temperature. The rate of flow in the heat exchanger tubes is 2 m/s. Coolant is passed through lines (10) at a rate just sufficient to remove the heat of crystallization and the heat added by the pumping energy. The rate of growth of the layer of crystalline material is 0.2 mm/min. When the frozen fraction in the heat exchangers is 90%, the residual liquid is discharged through line (7) and the unchanged melt contained in the compensating vessel (4) thus washes the crystalline surface. The system is filled with a melt of a composition corresponding to that of the crystalline product and the heat exchanger (9) is switched into circuit to cause melting of the crystalline product. The entire process is repeated 4 times, the crystalline product of one stage being used as the starting substance for the next stage. After such 4-stage crystallization, there is obtained caprolactam having a softening point of 69.0° C., a color number of 5 APHA, a content of volatile bases of 0.4 meq/kg and a permanganate absorption coefficient of 8.5.

[The permanganate absorption coefficient is the absorbance of a 1% caprolactam solution in water (50 ml or 100 ml of solution) after the addition of an N/100 potassium permanganate solution (1 or 2 ml) at 25° C. after 600 sec as compared with the same solution not containing caprolactam.]

EXAMPLE 2

Using the same apparatus and the same conditions as described in Example 1, the following substances were subjected to a single crystallization process:

acrylic acid, adipodinitrile, dicyanobutene, dimethyldithiophosphorylacetic acid methylamide, hexamethylenediamine, methylenediisocyanate and α-napththol.

Table 1 below lists the melt temperatures and starting concentrations of the products used and also the experimental conditions and the degree of purity achieved after a single crystallization operation.

TABLE 1

| Compound | Melt temperature $\theta_s$ °C. | Starting concentration $C_o$ % by weight | Rate of growth v mm/min | Rate of flow w m/sec | Final concentration $C_E$ % by weight |
|---|---|---|---|---|---|
| acrylic acid | 13 | 98 | 0.2 | 1.0 | 99.9 |
| adipodinitrile | 2.5 | 99 | 0.2 | 2.0 | 99.7 |
| dicyanobutene | 80 | 99 | 0.2 | 1.0 | 99.98 |
| dimethyldithio- | 40 | 85 | 0.1 | 1.5 | 95.1 |

TABLE 1-continued

| Compound | Melt temperature $\theta_s$ °C. | Starting concentration $C_0$ % by weight | Rate of growth v mm/min | Rate of flow w m/sec | Final concentration $C_E$ % by weight |
|---|---|---|---|---|---|
| phosphoryl aceto-methylamide 4,4'-diphenyl-methylene di-isocyanate | 38 | 92 | 0.1 | 1.5 | 99.1 |
| α-naphthene | 93 | 97 | 0.1 | 2.0 | 99.4 |
| hexamethylenediamine | 41 | UV = 3,800 | 0.2 | 1.0 | UV = 310 |

We claim:

1. An improved method of separation by fractional crystallization in which a liquid mixture is repeatedly passed in turbulent flow through an indirectly cooled crystallization zone, which crystallization zone is kept full of liquid mixture, and a layer of crystals is crystallized on the walls of the crystallization zone, the liquid remaining after deposition of the layer of crystals on the wall of the crystallization zone being removed, whereupon the surface of the layer of crystals is washed and the crystals are melted by passing through the crystallization zone a melt of similar composition to that of the crystals, wherein the improvement comprises:

carrying out the crystallization in a cascade of two crystallization zones the liquid mixture rising in the first zone and descending in the second zone, said zones being connected to a loop, maintaining the liquid mixture throughout the entire crystallization at a temperature equal to or less than the equilibrium temperature of said liquid mixture, wherein the ratio of rate of growth to mass transfer coefficient at the interface is controlled such that it remains constant or diminishes during crystallization and continuing the crystallization until a frozen fraction of from 70 to 98% is achieved, said frozen fraction being the percentage of the cross-section of the crystallization zone which is filled with the crystalline product.

2. A method as set forth in claim 1, wherein the layer of crystalline product is washed with a liquid mixture having a composition corresponding to that of the starting mixture.

3. A process as set forth in claim 1, wherein the crystallization zones have a diameter of from 1 to 4 cm and a l/d ratio of from 100:1 to 1000:1.

4. A process as set forth in claim 1, wherein the flow of the liquid mixture through the crystallization zone is from 0.2 to 6 m/sec.

5. A process as set forth in claim 1, wherein the growth rate of the layer of crystals in the crystallization zone is from 0.05 to 0.5 mm/min during crystallization.

* * * * *